United States Patent
Cranner et al.

(10) Patent No.: US 9,023,406 B2
(45) Date of Patent: May 5, 2015

(54) AMELIORATION OF THE APPEARANCE OF BRUISES

(71) Applicants: Bruce A. Cranner, Mandeville, LA (US); Anne-Marie T. Karp, New Orleans, LA (US); C. Scott Danos, Lilburn, GA (US)

(72) Inventors: Bruce A. Cranner, Mandeville, LA (US); Anne-Marie T. Karp, New Orleans, LA (US); C. Scott Danos, Lilburn, GA (US)

(73) Assignee: Dr. Holmquist Healthcare, LLC, Mandeville, LA (US)

( * ) Notice: Subject to any disclaimer, the term of this patent is extended or adjusted under 35 U.S.C. 154(b) by 5 days.

(21) Appl. No.: 13/815,359

(22) Filed: Feb. 25, 2013

(65) Prior Publication Data
US 2013/0210777 A1 Aug. 15, 2013

Related U.S. Application Data

(63) Continuation-in-part of application No. 13/029,551, filed on Feb. 17, 2011, now Pat. No. 8,399,032.

(51) Int. Cl.
| | |
|---|---|
| *A61K 47/10* | (2006.01) |
| *A61K 36/87* | (2006.01) |
| *A61K 36/899* | (2006.01) |
| *A61K 36/36* | (2006.01) |
| *A61K 36/48* | (2006.01) |
| *A61K 36/28* | (2006.01) |
| *A61K 8/34* | (2006.01) |
| *A61K 8/92* | (2006.01) |
| *A61Q 19/00* | (2006.01) |
| *A61K 9/00* | (2006.01) |
| *A61K 8/37* | (2006.01) |
| *A61Q 19/02* | (2006.01) |
| *A61K 47/44* | (2006.01) |

(52) U.S. Cl.
CPC ............... *A61K 8/345* (2013.01); *A61K 8/922* (2013.01); *A61Q 19/00* (2013.01); *A61K 9/0014* (2013.01); *A61K 47/10* (2013.01); *A61K 47/44* (2013.01); *A61K 8/375* (2013.01); *A61Q 19/02* (2013.01)

(58) Field of Classification Search
None
See application file for complete search history.

(56) References Cited

U.S. PATENT DOCUMENTS

| | | | | |
|---|---|---|---|---|
| 4,959,168 A | * | 9/1990 | Schroeck | 508/331 |
| 5,523,429 A | * | 6/1996 | Ghyczy | 554/4 |
| 6,017,986 A | * | 1/2000 | Burton | 524/313 |
| 7,078,056 B2 | | 7/2006 | Sessions | |

FOREIGN PATENT DOCUMENTS

JP 58058139 A * 4/1983

* cited by examiner

*Primary Examiner* — Chris R Tate
*Assistant Examiner* — Deborah Davis

(57) ABSTRACT

The present invention is directed to compositions and processes for their use that ameliorate the appearance of bruises, making them less cosmetically unappealing. The composition functions by acting both as a humectant and occlusive agent attracting water, returning the skin surface to a smooth state and holding water in place. The re-establishment of a homeostatic state in the skin results in a rapid dissipation of the negative cosmetic effects of the bruise on the skin.

11 Claims, No Drawings

AMELIORATION OF THE APPEARANCE OF BRUISES

RELATED APPLICATIONS

The present application is a continuation in part of a co-pending application of U.S. Ser. No. 13/029,551 which is in turn a divisional application of U.S. Ser. No. 12/248,155, filed Oct. 9, 2008, and titled, "Bruise Amelioration Composition and Method of Use," which is a continuation-in-part application of U.S. Ser. No. 11/441,878, filed May 26, 2006, and titled, "Bruise Amelioration Composition and Method of Use." The contents of U.S. Ser. Nos. 13/029,551; 12/248,155 and 11/441,878 are expressly incorporated by reference into the present application.

FIELD OF THE INVENTION

The present invention is directed to compositions and processes for their use that ameliorate the appearance of bruises, making them less cosmetically unappealing. The composition functions by acting both as a humectant and occlusive agent attracting water, returning the skin surface to a smooth state and holding water in place. The re-establishment of a homeostatic state in the skin results in a rapid dissipation of the negative cosmetic effects of a bruise on the skin.

The ability to make a composition that contains glycerin, a humectant, and a triglyceride with a specified iodine value (which is a measure of unsatutation), provides a unique, heretofore-unappreciated composition that has stability and provides a dual mechanism product that reduces the appearance of bruises.

BACKGROUND OF THE INVENTION

A bruise is a condition caused by distress to tissue that causes capillaries to break under the skin, allowing blood to escape and build up. As time progresses, blood seeps into the surrounding tissues, causing the bruise to darken and spread. The damaged capillary endothelium releases endothelin, a hormone that causes narrowing of the blood vessel to minimize bleeding. As the endothelium is destroyed, the underlying von Willebrand factor is exposed and initiates coagulation, which creates a temporary clot to plug the wound and eventually leads to restoration of normal tissue.

During this time, larger bruises may change color due to the breakdown of hemoglobin from within escaped red blood cells in the extracellular space. The striking colors of a bruise are caused by the phagocytosis and sequential degradation of hemoglobin to biliverdin to bilirubin to hemosiderin, with hemoglobin itself producing a red-blue color, biliverdin producing a green color, bilirubin producing a yellow color, and hemosiderin producing a golden-brown color. As these products are cleared from the area in the normal healing process of the body, the bruise disappears. Often the underlying tissue damage has been repaired long before this process is complete.

Because the color produced by bruising is cosmetically unappealing, consumers want to minimize the appearance by application of cosmetic products. Some cosmetic products provide color to the skin to hide the bruise. This approach does not help correct the problem, but rather simply covers it up. Providing color to the skin is not only is a short-term approach, it can also lead to unacceptable consumer response if the color in uneven.

The other approach is to provide a topical product that improves the appearance of the bruise. While not wanting to be held to one specific theory, the best topical product candidates will allow for the re-establishment of the homeostatic state that was present before the bruise-causing incident. This results in an amelioration of the appearance of the bruise. Specifically, the skin needs to be returned as quickly as possible to the natural state of water balance present before the incident that caused the bruising. For the purposes of this invention, references to "skin" encompass the epidermis, dermis, and proximal tissues below the skin where a bruise may appear.

There are two known methods of returning the skin to its normal state of hydration: (a) topical application of occlusives (water insoluble materials work by forming a thin film on the surface of the skin to prevent any loss of moisture, the best known of these is Vaseline); and, (b) humectants which are materials that are water soluble and attract water from the air to moisturize the skin.

One class of important occlusives is triglycerides. Triglyceride is an ester derived from glycerol and three fatty acids. They are the main constituents of vegetable oil and animal fats. As one applies oily materials (occlusives) to the external layers of the skin, the skin becomes softer and more pliable. This reduces evaporation. These materials inhibit transepidermal water loss (keep water in). They are water insoluble materials.

Humectants, like glycerin, attract water to the skin. These materials are very water-soluble.

The problem with these two approaches is that they have heretofore been mutually exclusive; that is, if only a humectant is used to attract water to the skin, it can too easily be removed from the skin by water. Occlusive materials, along, block the hydrating properties we require to ameliorate the appearance of bruises.

To further thwart the search for a truly multifunctional approach, oil and water do not mix. This lack of solubility makes the possibility of formulating a truly multi-faceted formulation to reduce the appearance of bruises impossible.

U.S. Pat. No. 7,078,056 is typical of the state of the art. It states, "The present invention concerns a method of treating a patient to attenuate, and in some cases eliminate, symptoms (e.g., pain, inflammation, bruising, etc.) normally caused or potentiated by the activation of the nociceptive system through the use of a composition including at least a hydrophilic foam substrate, a hydrophilic agent capable of absorbing water, and a wetting agent to the surface of the skin. The composition is applied to the surface of the skin in an amount and at a location sufficient to attenuate the response of the nociceptors to noxious stimuli." The key to this reference is it uses a totally hydrophilic treatment system, clearly avoiding hydrophobic materials that lock in the moisture and smooth the damaged skin.

There has been a long felt need to produce a composition that can be used to ameliorate the appearance of bruises.

THE INVENTION

Object of the Invention

It is the object of the present invention to provide a composition that comprises a carefully selected level of glycerin and of triglyceride to provide a serum or gel that, when applied to skin, provides an occlusive barrier to the skin. This composition also contains humectants (water-soluble components) that can be absorbed into the skin in a stable thick dispersion.

Another object of the present invention is to provide a process for ameliorating the cosmetic appearance of bruises.

This is accomplished by applying to the skin the concentration of the composition of the present invention. Other objectives will become clear as one reads the specification.

All temperatures are degrees centigrade, and all percentages are percentage by weight.

SUMMARY OF THE INVENTION

The present invention is directed to a thick dispersion of glycerin and triglyceride wherein the concentration of glycerin ranges from 80 to 99% by weight and the concentration of triglyceride ranges from 1 to 20% by weight. The triglyceride must have an iodine value of between 100 and 160 mg KOH/gram to provide a stable dispersion.

This dispersion contains both a humectant (glycerin) and an occlusive agent (triglyceride) that functions to ameliorate the appearance of bruises.

DETAILED DESCRIPTION OF THE INVENTION

A composition that comprises:
(a) Between 80 and 99% by weight of glycerin, and
(b) Between 1 and 20% of a triglyceride having an iodine value of between 100 and 160 mg KOH/gm.

A process for ameliorating the appearance of bruising, which comprises contacting the skin with an effective ameliorating concentration of a composition, which comprises:
(a) Between 80 and 99% by weight of glycerin, and
(b) Between 1 and 20% of a triglyceride having an iodine value of between 100 and 160 mg KOH/gm.

In a preferred embodiment the concentration of glycerin ranges from 90-99% by weight and the concentration of triglyceride ranges from 1-10% by weight.

In a more preferred embodiment the concentration of glycerin ranges from 95-99% by weight and the concentration of triglyceride ranges from 1-5% by weight.

The present invention also envisions the addition of optional ingredients including but not limited to Vitamin E, Vitamin C, Vitamin D, retinol, flavonoids, antioxidants, anti-acne including azelic acid, alpha hydroxy acids including glycolic acid, beta hydroxy acids including salicylic acid. These materials are either added at a monograph level or at 1-5% by weight. When incorporated into the compositions of the present invention these materials remain on the skin for a longer period of time than is observed when they are applied from traditional water containing systems.

EXAMPLES

Glycerin
Glycerin is an item of commerce. It conforms to the following structure:

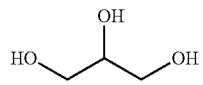

Glycerin has an IUPAC name of 1,2,3-triol and a CAS number of 58-81-5.

Iodine Value
We have surprisingly found that triglycerides with a specific level of unsaturation provide the stable dispersion we seek for the compositions of the present invention. Iodine value (IV) is a measure of the unsaturation present in particular chemical. The higher the iodine value, the more double bonds are in the molecule. The preferred method is known as the Wijs procedure, it is commonly used.

Iodine value is a measure of the total number of double bonds present in fats and oils. It is generally expressed in terms of "the number of grams of iodine that will react with the double bonds in 100 grams of fats or oils".

Oils with a high iodine value contain a greater number of double bonds than low iodine value oils. Edible oils with high IV are usually less stable and more susceptible to oxidation.

The American Oil Chemists' Society (AOCS) recommends the use of ASTM method D1959-97, also known as the Wijs method, for determination of IV. The method involves the addition of Wijs solution to the sample, after which it is allowed to stand in the dark. The reaction is complete after approximately 30 min, at which time potassium iodide is added. The liberated iodine is then titrated with sodium thiosulfate, using a standard starch solution as the indicator.

Examples

Triglycerides

Natural oils chemically are triglycerides. Triglyceride is an ester derived from glycerol and three fatty acids conforming to the following structure:

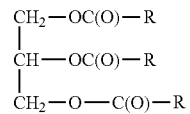

The triglycerides that are useful in making the compositions of the present invention R are over 50% by weight C18. The triglycerides are also unsaturated. The level of unsaturation is measured by iodine value that is expressed in mg KOH/gm.

We have found that the iodine value needed to make the compounds of the present invention needs to be over 100 mg KOH /gram and less than 160 mg KOH/gm. This is because this specific type of triglyceride, when blended with glycerin in the range of 1 to 20% by weight of the triglyceride, results in a thick stable dispersion. It is this thick dispersion that results in a truly multifunctional composition.

While not wanting to be bound by a particular theory, the applicants believe that the iodine value of these triglycerides, which is an indication of the double bonds present in the oil when properly selected, allows for stable dispersions of the triglyceride in the glycerin. Additionally and very importantly, the presence of the triglyceride in the glycerin over the specifically specified range results in a composition that provides both humectant properties and minimized transepidermal water loss (occlusive properties), both of which aid in returning the skin to the state which existed before the bruise occurred, ameliorating the appearance of the bruise. It is the critical combination of (a) the concentration of the glycerin relative to the triglyceride, and (b) the amount of unsaturation of the triglyceride as measured by iodine value, that provides the unique properties required to ameliorate the appearance of bruises.

The triglycerides useful in the preparation of the compositions of the present invention are natural products and are as follows:

| Example | Product | Genus/species | Iodine Value (KOH/gm) |
|---|---|---|---|
| 1 | Sunflower Seed Oil | Helianthus annuus | 130 |
| 2 | Apricot Kernel Oil | Prunus armeniaca | 102 |
| 3 | Argan Oil | Argania spinosa | 100 |
| 4 | Cottonseed Oil | Gossypium hirsutum | 108 |
| 5 | Rice Bran Oil | Oryza sativa | 105 |
| 6 | Wheat germ Oil | Triticum vulgare | 130 |
| 7 | Vernonia Oil | Vernonia galamensis | 106 |
| 8 | Poppy Seed Oil | Populus nigra | 138 |
| 9 | Grape Seed Oil | Vitis vinifera | 135 |
| 10 | Sesame Oil | Sesamum indicum | 110 |
| 11 | Sweet Almond Oil | Prunus amygdalus dulcis | 102 |
| 12 | Soybean Oil | Glycine soja | 130 |
| 13 | Safflower Oil | Carthamus tinctorius | 145 |
| 14 | Walnut Oil | Juglans regia | 150 |
| 15 | Evening Primrose Oil | Denothera biennis | 152 |
| 16 | Olive Oil | Olea eruopaea | 84 |

In order to demonstrate the effectiveness of the compositions of the present invention, several dispersions were made using a variety of triglycerides.

General Procedure

The specified number of grams of the specified triglyceride (example 1-15) was added to glycerin under agitation over a range of concentrations, under good agitation. The material was mixed for about 30 minutes, whereupon it was passed through a Silverson homogenizer. After 30 minutes at room temperature the product was evaluated for the presence of a separation into an oil and water phase.

Example 16

| Material | % wt | Grams |
|---|---|---|
| Glycerin | 98.0 | 980.0 |
| Example 15 | 2.0 | 20.0 |

A translucent thick dispersion was obtained that was stable overnight.

Example 17

| Material | % wt | Grams |
|---|---|---|
| Glycerin | 90.0 | 900.0 |
| Example 15 | 10.0 | 100.0 |

A less translucent uniform thick dispersion was obtained that was stable overnight.

Example 18

| Material | % wt | Grams |
|---|---|---|
| Glycerin | 80.0 | 800.0 |
| Example 15 | 20.0 | 200.0 |

An opaque thick dispersion was obtained that was stable overnight.

Example 19

Control Example—not of the Present Invention

| Material | % wt | Grams |
|---|---|---|
| Glycerin | 70.0 | 700.0 |
| Example 15 | 30.0 | 300.0 |

A product that split into two layers was observed.

Hydrophobicity

Despite the fact that the formulation was predominantly glycerin (water soluble), the compositions rendered a glass substrate hydrophobic, indicating we have indeed discovered a way to keep hydrophilic humectants (glycerin) on the skin in a hydrophobic formulation, thus providing both mositurization by humectancy and by occlusive mechanisms.

Example 16-19 were evaluated using a microscope slide dip process (MSDP). In this test a 200 grams of the composition are placed into a 400 ml beaker and microscope slide is dipped into the composition and allowed to remain 5 minutes at room temperature, whereupon the appearance of the slide is evaluated. The slide is removed and left exposed to the air for 5 minutes. A drop of water is then added and the slide is evaluated as the $2^{nd}$ evaluation.

$1^{st}$ Evaluation Scoring System

0 No coating
1 Little coating
2 Some coating
3 Uniform coating (thin)
4 Uniform coating (intermediate)
5 Thick uniform coating $2^{nd}$ Evaluation Scoring System 0 No effect
1 Water runs off
2 Minimal drop formation
3 Flat water droplets (small)
4 Flat water droplets (medium)
5 Stable water droplet on surface Evaluation of MSDP Results

| Example | $1^{st}$ Evaluation | $2^{nd}$ Evaluation | Additive Effect |
|---|---|---|---|
| 16 | 3 | 4 | 7 |
| 17 | 4 | 5 | 9 |
| 18 | 5 | 4 | 9 |
| 19 | 0 | 0 | 0 |
| Glycerin alone | 0 | 0 | 0 |

The composition with 90% glycerin by weight is tenacious to water and hydrophobic, providing the two types of moisturization mechanisms, occlusive film minimizing transepidermal water loss and humectancy attracting and retaining water.

Human Forearm Test (HFT)

The following process was performed on human forearms using the following procedure:

0.5 ml of compositions was applied to the forearm and rubbed on the skin of the forearm to an area the size of a quarter. After 5 minutes a drop of water was applied.

Evaluation of HFT Results

| Example | 1st Evaluation | 2nd Evaluation | Additive Effect |
|---|---|---|---|
| 16 | 4 | 4 | 8 |
| 17 | 4 | 4 | 8 |
| 18 | 4 | 4 | 8 |
| 19 | 0 | 0 | 0 |
| Glycerin alone | 0 | 0 | 0 |

Compositions of the Present Invention

The compositions of the present invention are prepared using the procedure described above.

| Example No. | Glycerin Weight (gm) | Triglyceride Example No. | Triglyceride Weight (gm) |
|---|---|---|---|
| 20 | 99 | 1 | 1 |
| 21 | 95 | 2 | 5 |
| 22 | 90 | 3 | 10 |
| 19 | 80 | 4 | 20 |
| 20 | 84 | 5 | 16 |
| 21 | 91 | 6 | 9 |
| 22 | 85 | 7 | 15 |
| 23 | 83 | 8 | 17 |
| 24 | 89 | 9 | 11 |
| 25 | 90 | 10 | 10 |
| 26 | 99 | 11 | 1 |
| 26 | 97 | 12 | 3 |
| 28 | 95 | 13 | 5 |
| 29 | 98 | 14 | 2 |
| 30 | 98 | 15 | 2 |
| 31 | 95 | 15 | 5 |
| 32 | 99 | 15 | 1 |

Compositions wherein the concentration of glycerin ranges from 95-99% by weight, and triglyceride ranges from 1-5%, are clear compositions.

Compositions wherein the concentration of glycerin ranges from 90-94% by weight, and triglyceride ranges from 6-10%, are translucent stable dispersions.

Compositions wherein the concentration of glycerin ranges from 80-89% by weight, and triglyceride ranges from 11-20%, are stable opaque dispersions.

The compositions of the present invention when applied to the skin can result in improvement to the cosmetic appearance of skin and the amelioration of the appearance of bruises.

Composition Outside the Scope of the Invention

A composition using oil outside the scope of the current invention for iodine value was tested as a comparative example. Olive Oil was chosen since it has an iodine value of 84 mg KOH/gm. It is Example 16.

| Material | % wt | Grams |
|---|---|---|
| Glycerin | 90.0 | 900.0 |
| Example 16 | 10.0 | 100.0 |

A product that split into two layers was observed.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove, but rather that the claims be construed as encompassing all the features of patentable novelty which reside in the present invention, including all features which would be treated as equivalents thereof by those skilled in the art to which the invention pertains.

The invention claimed is:

1. A composition for ameliorating the appearance of skin bruising that comprises:
   (a) between 80 and 99% by weight of glycerin having the following structure;

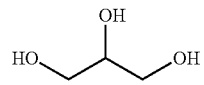

and
   (b) between 1 and 20% of a triglyceride having an iodine value of between 100 and 160 mg KOH/gm.

2. The composition of claim 1 wherein the concentration of glycerin ranges from 85-95% by weight and the concentration of triglyceride ranges from 5-15% by weight.

3. The composition of claim 1 wherein the concentration of glycerin ranges from 80-95% by weight and the concentration of triglyceride ranges from 5-20% by weight.

4. The composition of claim 1 wherein the iodine value of said triglyceride ranges from between 105 and 140 mg KOH/gm.

5. The composition of claim 1 wherein the iodine value of said triglyceride ranges from between 125 and 155 mg KOH/gm.

6. A process for the amelioration of the appearance of skin bruising in a subject, which comprises contacting the skin with an effective ameliorating concentration of a composition, wherein said composition comprises:
   (a) between 80 and 99% by weight of glycerin having the following structure:
   having the following structure:

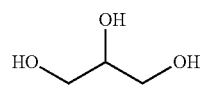

and
   (b) between 1 and 20% of a triglyceride having an iodine value of between 100 and 160 mg KOH/gm.

7. The process of claim 6 wherein the concentration of glycerin ranges from 85-95% by weight and the concentration of triglyceride ranges from 5-15% by weight.

8. The process of claim 6 wherein the concentration of glycerin ranges from 80-95% by weight and the concentration of triglyceride ranges from 5-20% by weight.

9. The process of claim 6 wherein the iodine value of said triglyceride ranges from between 105 and 140 mg KOH/gm.

10. The process of claim 6 wherein the iodine value of said triglyceride ranges from between 125 and 155 mg KOH/gm.

11. The process of claim 6 additionally containing additives selected from the group consisting of Vitamin E, Vitamin C, Vitamin D, retinol, flavonoids, antioxidants, anti-acne including azelic acid, alpha hydroxy acids including glycolic acid, beta hydroxyl acids including salicylic acid.

* * * * *